United States Patent [19]

Meilland

[11] Patent Number: Plant 7,021

[45] Date of Patent: Sep. 12, 1989

[54] ROSE PLANT—MEIRUTRAL VARIETY

[75] Inventor: Alain A. Meilland, Antibes, France

[73] Assignee: The Conard-Pyle Company, West Grove, Pa.

[21] Appl. No.: 241,377

[22] Filed: Sep. 6, 1988

[51] Int. Cl.[4] ..... A01H 5/00
[52] U.S. Cl. ..... Plt./10
[58] Field of Search ..... Plt. 10

*Primary Examiner*—Robert E. Bagwill

*Attorney, Agent, or Firm*—Burns, Doane, Swecker & Mathis

[57] ABSTRACT

A new and distinct variety of Miniature rose plant is provided which abundantly forms on a continuous basis attractive long lasting semi-double blossoms. The blossoms are currant red in coloration and well retain this coloration upon the passage of time. The new variety is well adapted to greenhouse forcing under low light conditions and can be used as an attractive pot plant for indoor or outdoor decoration.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) of the new variety was the Meichanso variety (non-patented in the United States). The Meichanso variety is sometimes known as the Parador variety. The male parent (i.e., the pollen parent) was the Mogral variety (non-patented in the United States). The parentage of the new variety can be summarized as follows:

Meichanso × Mogral.

The seeds resulting from the above pollination were sown and 84 plantlets were obtained which were physically and biologically different from each other. Selective study resulted in the identification of a single plant of the new variety.

The new variety meets well the needs of the horticultural industry for all uses, and is particularly well suited for use as a flowering pot plant for indoor or outdoor decoration.

It was found that the new variety of Miniature rose plant of the present invention possesses the following combination of characteristics:

(a) abundantly and continuously forms attractive long lasting semi-double blossoms which are currant red in coloration with such coloration being well retained during the life of the blossoms,
(b) is particularly well suited for greenhouse forcing as a pot plant under low light conditions,
(c) exhibits a vigorous growth habit, and
(d) is not particularly affected by cryptogamic diseases.

The buds and blossoms advantageously retain the attractive currant red coloration during the time of blooming and do not assume a purple-red coloration towards the end of blooming.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meirutral variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and observed during February while growing on their own roots in a greenhouse at Cannet-des-Maures, France.

DETAILED DESCRIPTION

Figures 1, 2, 3, 4, 5, 6, 7, 8, 9, 10, 11, 12, 13, 14, 15, 16:
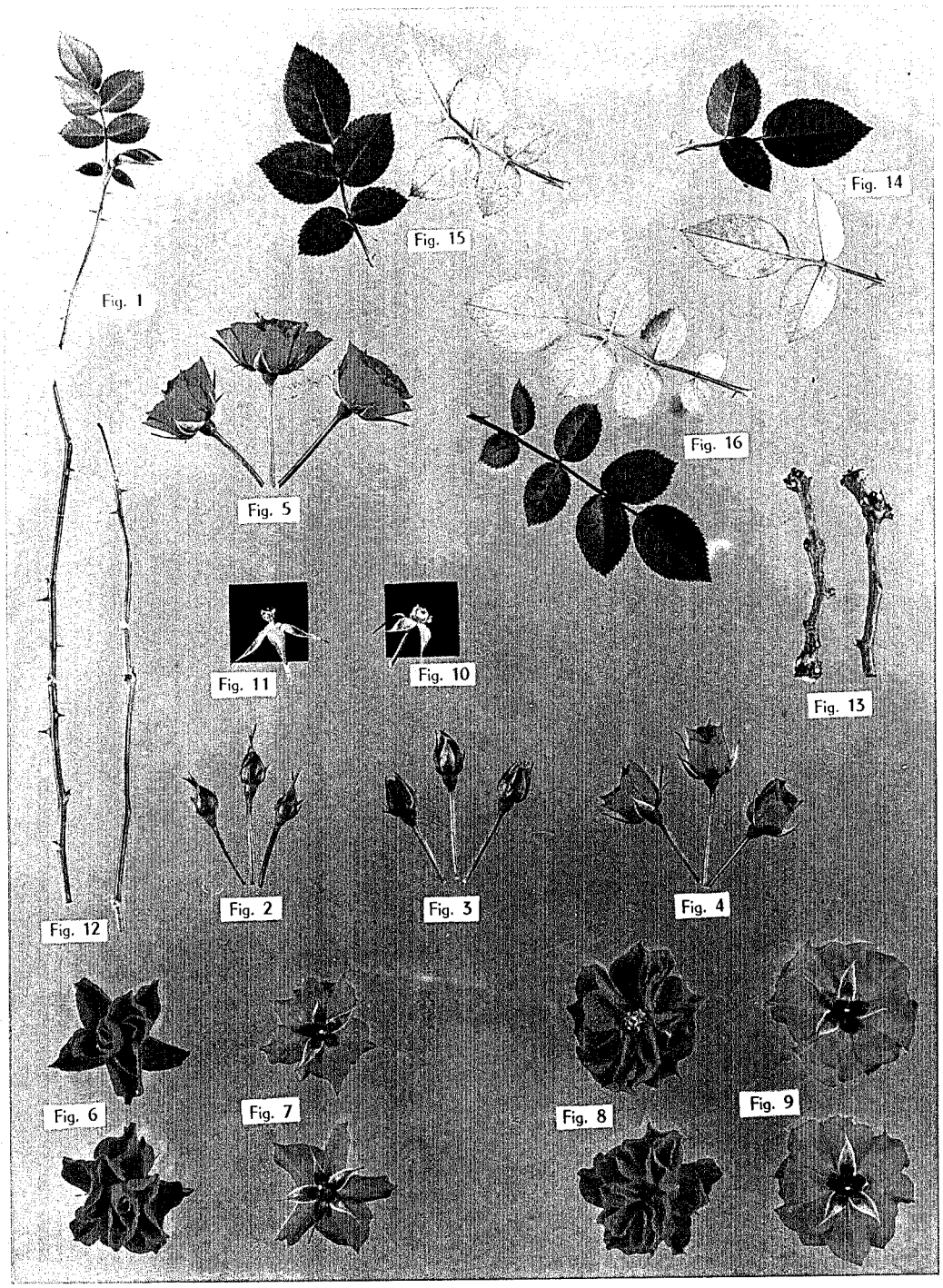
FIG. 1 illustrates a specimen of a young shoot with leaves.
FIG. 2 illustrates specimens of three floral buds before the opening of the sepals.
FIG. 3 illustrates specimens of three floral buds at the opening of the sepals.
FIG. 4 illustrates specimens of three floral buds at the opening of the petals.
FIG. 5 illustrates specimens of three flowers in the course of opening.
FIG. 6 illustrates specimens of two open flowers—plan view—obverse.
FIG. 7 illustrates specimens of two open flowers—plan view—reverse.
FIG. 8 illustrates specimens of two fully open flowers immediately prior to petal drop—plan view—obverse.
FIG. 9 illustrates specimens of two fully open flowers immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates specimens of two flowering stems.
FIG. 13 illustrates specimens of two portions of a main branch.
FIG. 14 illustrates specimens of leaves with three leaflets—(upper (top) and under (bottom) surfaces.
FIG. 15 illustrates specimens of leaves with five leaflets—upper (left) and under (right) surfaces.
FIG. 16 illustrates specimens of leaves with seven leaflets—plan view—upper (bottom) and under (top) surfaces.

The chart used in the identification of the colors is that of The Royal Horticultural Society (R.H.S. Colour Chart). The terminology which precedes reference to the chart has been added to indicate the corresponding color in more common terms. The description is based on two year old specimens of the new variety during February while growing on their own roots in a greenhouse at Cannet-des-Maures, France.

Class: Miniature.

Plant:

*Height.*—Approximately 20 to 25 cm.

*Habit.*—Bushy.

Branches:

*Color.*—Young stems: light green, Green Group 143C, more or less overlaid with reddish coloration. Adult wood: medium green, Green Group 143B.

Leaves:

*Stipules.*—Adnate, pectinate, narrow and regular.

*Petioles.*—Upper surface: channeled, reddish brown on young foliage and medium green on adult foliage. Under surface: light green, with some slightly glandular edges.

*Leaflets.*—Number: 3, 5 and 7 (most often). Shape: elliptic. Serration: single and regular. Texture: consistent. General appearance: dense foliage which is semi-dull. Color (young foliage): Upper surface: light green, Green Group 143B, overlaid with reddish coloration. Under surface: medium green, 137D more or less exhibiting a reddish tint. Color (adult foliage): Upper surface: medium green, Green Group 143A. Under surface: medium green, Green Group 137D.

Inflorescence:

*Number of flowers.*—Commonly 1 to 2 per stem.

*Peduncle.*—Light green, narrow, rigid, sometimes with small glands, approximately 4 cm. in length on average.

*Sepals.*—Upper surface: tomentose and greenish in coloration. Under surface: light green in coloration, more or less overlaid with a reddish tint, the outer sepals have appendiculated edges.

*Buds.*—Shape: oval. Length: approximately 1 to 1.5 cm. on average. Size: small. Color upon opening: Upper surface: currant red, Red Group 46A. Under surface: currant red, Red Group 46A (dull).

*Flower.*—Shape: semi-double, assumes the configuration of a flattened cup. Diameter: approximately 4 to 5 cm. on average. Color (when opening begins): Upper surface: currant red, Red Group 46A. Under surface: currant red, Red Group 46A. Color (when partially open): Upper surface: currant red, Red Group 46A. Under surface: currant red, Red Group 46A. Color (at end of opening): Upper surface: currant red, Red Group 46A. Under surface: currant red, Red Group 46A. Fragrance: none. Lasting quality: long. Petal drop: good. Petal number: approximately 20 to 22 on average. Petal texture: consistent. Petal form: wide oval on the outside and narrow oval with a sharply pointed tip on the inside. Stamen number: approximately 60 to 64 on average. Anthers: normal, ochre. Filaments: fuchsine in coloration and of irregular heights. Pistils: approximately 41 to 44 on average. Stigmas: straw colored, of approximately the same height as the stamens. Styles: fuchsine in coloration and of irregular heights. Receptacle: light green in coloration, smooth, and in a longitudinal section it is narrow and in the shape of a pitcher.

Development:

*Vegetation.*—Vigorous.

*Blooming.*—Abundant and continuous.

*Resistance to diseases.*—Very good.

*Aptitude to bear fruit.*—Normal.

*Aptitude to forcing.*—Well adapted to greenhouse forcing as a pot plant under low light conditions.

I claim:

1. A new and distinct variety of Miniature rose plant characterized by the following combination of characteristics:

(a) abundantly and continuously forms attractive long lasting semi-double blossoms which are currant red in coloration with such coloration being well retained during the life of the blossoms, (b) is particularly well suited for greenhouse forcing as a pot plant under low light conditions, (c) exhibits a vigorous growth habit, and (d) is not particularly affected by cryptogamic diseases, substantially as herein shown and described.

* * * * *